United States Patent
Feldgiebel

(10) Patent No.: US 6,860,865 B1
(45) Date of Patent: Mar. 1, 2005

(54) COMPRESSION BANDAGE

(75) Inventor: Rainer Feldgiebel, Neuwied (DE)

(73) Assignee: Lohmann GmbH & Co. KG, Neuwied (DE)

( * ) Notice: Subject to any disclaimer, the term of this patent is extended or adjusted under 35 U.S.C. 154(b) by 0 days.

(21) Appl. No.: 09/700,048

(22) PCT Filed: Apr. 19, 1999

(86) PCT No.: PCT/EP99/02608

§ 371 (c)(1),
(2), (4) Date: Jul. 10, 2001

(87) PCT Pub. No.: WO99/56683

PCT Pub. Date: Nov. 11, 1999

(30) Foreign Application Priority Data

May 7, 1998 (DE) ..................... 298 08 232 U

(51) Int. Cl.7 ............................................. A61L 15/00
(52) U.S. Cl. .............................. 602/75; 602/76; 602/60
(58) Field of Search .......................... 602/5, 23, 27–29, 602/61, 65, 66, 62, 75, 76, 60

(56) References Cited

U.S. PATENT DOCUMENTS

| 2,687,723 A | 8/1954 | Stern |
| 3,605,122 A | 9/1971 | Myers |
| 4,367,733 A | 1/1983 | Stromgren |
| 5,139,479 A | 8/1992 | Peters |
| 5,620,413 A | 4/1997 | Olson |
| 5,676,641 A | 10/1997 | Arensdorf et al. |

FOREIGN PATENT DOCUMENTS

| EP | 0 286 554 | 10/1988 |
| GB | 295 886 | 8/1928 |
| GB | 680 670 | 10/1952 |

Primary Examiner—Nicholas D. Lucchesi
Assistant Examiner—Lalita M. Hamilton
(74) Attorney, Agent, or Firm—D. Peter Hochberg; Katherine R. Vieyra; Sean Mellino

(57) ABSTRACT

A compression bandage for supporting the tissue in the area between foot and knee, for example for treating venous and/or lymphatic swellings, is characterized in that it is designed with a ready-made foot part.

5 Claims, 4 Drawing Sheets

COMPRESSION BANDAGE

BACKGROUND OF THE INVENTION

The invention relates to a compression bandage for supporting the tissue in the area between foot and knee, for example for treating venous and/or lymphatic swellings.

DESCRIPTION OF THE PRIOR ART

In the diagnostic indication of venous edema or lymphatic edema, the limb is swollen because of accumulations of fluid. These swellings have to be controlled and gradually eliminated by, among other things, application of a compression bandage, with the circumference of the calf becoming smaller as the swelling reduces. This phenomenon is referred to medically as the acute phase. In this acute phase, treatment with compression dressings is principally recommended. On account of the difficulties which have to be overcome when applying short-stretch compression dressings (for example there must be an exactly definable preliminary tensioning of the stretch compression bandage), the bandage must in most cases be applied by trained personnel or by the doctor, because the winding-on of the bandage is considered too difficult for the patient. Above all, winding the bandage around the front part of the foot and around the heel is considered particularly difficult.

After the swelling of the limb has reduced from the acute phase, a compression stocking is in most cases prescribed in the subsequent maintenance phase. This compression stocking must be tailor-made in about 40% of cases, for which reason the stocking is extremely expensive.

The aforementioned venous and lymphatic disorders are mostly chronic conditions which in some instances have to be treated for life. At present, acute phase and maintenance phase alternate in most patients since, particularly in the summer months, or in the event of poor compliance by the patient, the affected limbs swell up considerably for a time. This has the serious disadvantage that the prescribed compression stocking then no longer fits and has to be replaced at least temporarily by a compression dressing which has to be applied by trained personnel.

SUMMARY OF THE INVENTION

The object of the invention is to make available an improved compression bandage which, while overcoming the abovementioned disadvantages and difficulties, does not have to be wound around the front of the foot and around the heel and thus puts the patient advantageously in the position of being able to apply the compression bandage independently and therefore also with an individual feel for the compression, at least without medical or specially trained assistance, and in addition the patients require only one product for a wide variety of states of swelling of the limb, both for the acute phase and also for the maintenance phase.

This object is achieved in a compression bandage of the type specified in the preamble of claim 1 by virtue of the fact that it is designed with a ready-made foot part.

The compression bandage according to the invention with ready-made foot part represents an advantageous, readily adjustable combination between compression stocking and compression dressing. Thus, upon application, the difficulty which previously existed when winding the bandage around the front of the foot and around the heel is overcome, these areas being the most difficult areas of the body to bandage. Since the patient, after pulling on the stocking part in the manner of a normal stocking, is now able, without medical or specially qualified assistance, to wind the bandage around the rest of the lower leg area between the ankle region and the knee, and to do so independently and with an individually adjusted compression effect, straightforward handling of the compression bandage is advantageously realized, and it can be applied on varying calf circumferences and without help from others. Thus, it is also possible to dispense with application of a compression stocking, and instead the compression bandage according to the invention can be used in all states of swelling and throughout the entire duration of treatment.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DESCRIPTION OF THE PREFERRED EMBODIMENT

Figure 1A:
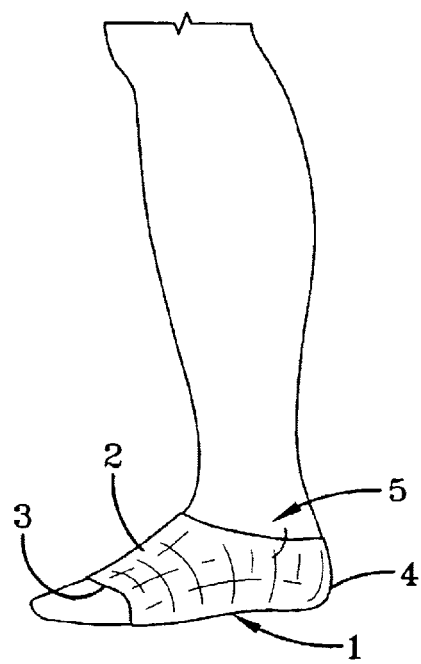
FIG. 1a is a perspective view of a human leg from foot to knee and the compression bandage without the compression dressing.
Figure 1B:
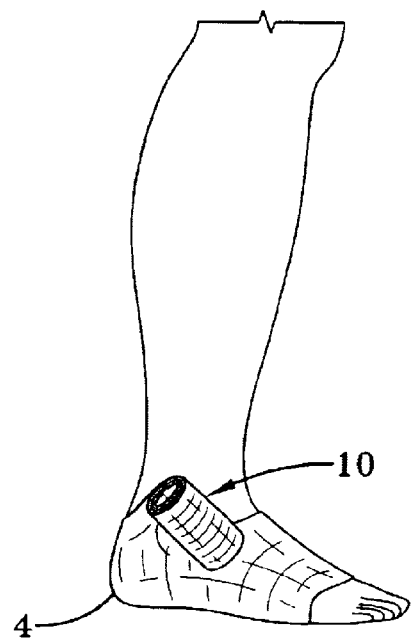
FIG. 1b is a perspective view of a human leg from foot to knee and the compression bandage with a first phase of application of the compression dressing without winding around the heel.
Figure 1C:
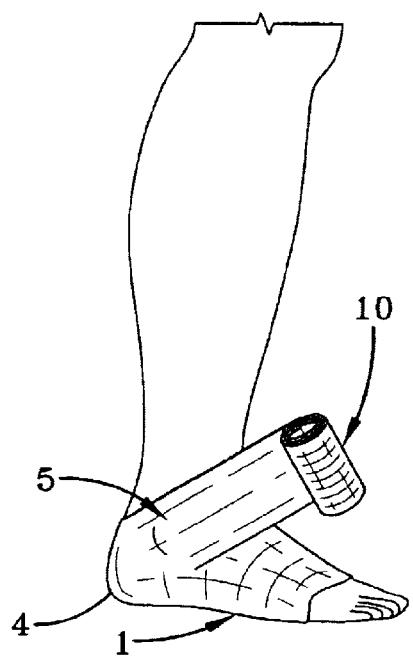
FIG. 1c is a perspective view of a human leg from foot to knee and the compression bandage with a second phase of application of the compression dressing without winding around the heel.
Figure 1D:
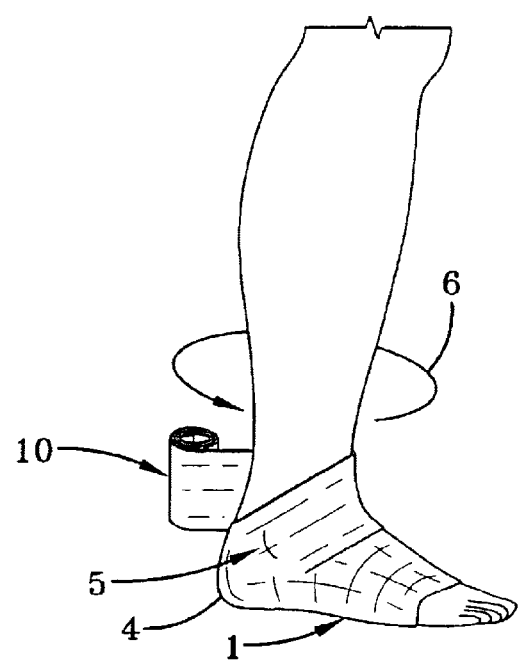
FIG. 1d is a perspective view of a human leg from foot to knee and the compression bandage with a third phase of application of the compression dressing without winding around the heel.
Figure 1E:
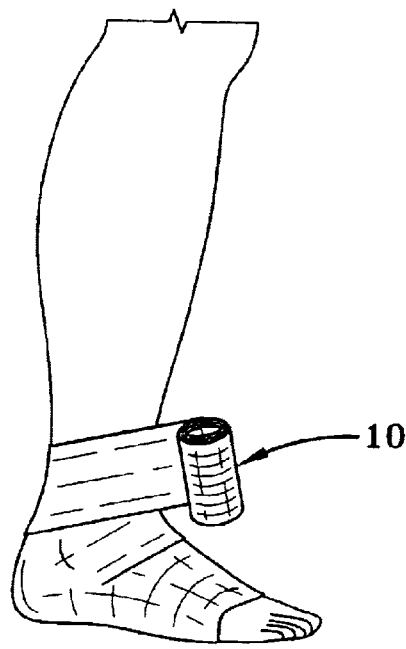
FIG. 1e is a perspective view of a human leg from foot to knee and the compression bandage with a fourth phase of application of the compression dressing without winding around the heel.

In one embodiment, the foot part has a preferably circular-knitted compression middle part with, at one end, an open front without toe inclusion and, at the other end, a knitted-in heel, and a compression bandage, preferably with a length of 3 to 7 meters, adjoins or attaches to the upper edge of the foot part.

It is thus possible for the foot part to end in the area of the ankle, specifically either below or above the latter.

The advantage of the compression bandage according to the invention is that it represents a combination of compression stocking and compression bandage.

The compression bandage according to the invention is applied as follows:

- The foot part is pulled onto the foot in the manner of a stocking,
- The dressing arranged on the foot part is wound on starting at the ankle area, without going around the heel again, preferably with half coverage of the dressing turns, spirally or in figures of eight, and ending approximately two finger widths below the hollow of the knee with a circular turn.

Finally, the compression bandage according to the invention can be applied, after the foot part has been pulled on, by winding the bandage twice around the heel and preferably with ⅓ coverage to a point below the hollow of the knee, ending with a circular turn, and with individually adjustable compression tension around the lower leg.

Further details, features and advantages of the invention will emerge from the following explanation of a number of illustrative embodiments represented diagrammatically in the drawings, in which:

FIGS. 1a through 1f show a human leg in a perspective view, from foot to knee, with a sequence of work phases for application of the compression bandage according to the invention without further winding around the heel;

FIGS. 2a through 2e show a leg, in a perspective view, with successive work phases for application of the compression bandage with winding around the heel.

FIG. 1a shows the foot part of the compression bandage according to the invention with a preferably circular-knitted compression middle part 2 with, at one end, an open front 3 without toe inclusion, and, at the other end, a knitted-in heel 4.

Subsequent FIGS. 1b through 1f show that a compression bandage 10 measuring 3 to 7 m in length adjoins the upper edge of the foot part 1.

The foot part 1 ends in the area 5 of the ankle, specifically either below or above the latter, in general preferably above it.

From the views in FIGS. 1a through 1f, and likewise from FIGS. 2a through 2e, it is clearly evident that the compression bandage according to the invention is a combination of compression stocking and compression bandage.

Figure 1F:
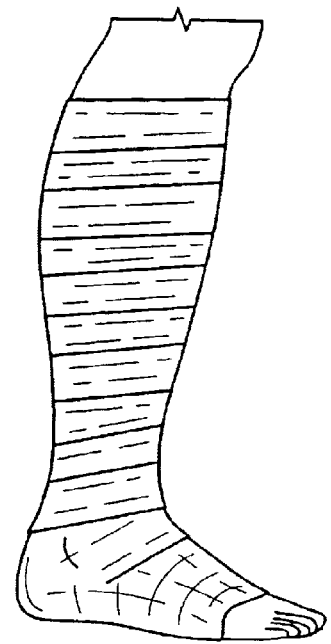
FIG. 1f is a perspective view of a human leg from foot to knee and the compression bandage with completed application of the compression dressing without winding around the heel.
Figure 2I:
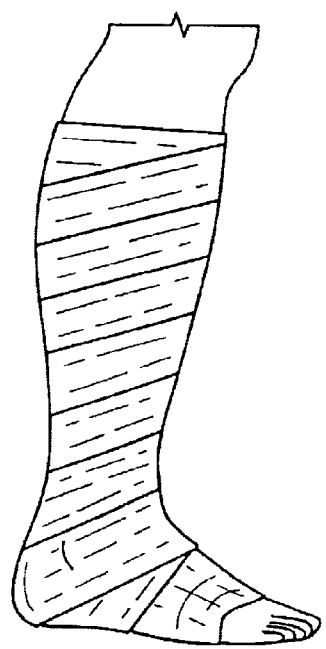
FIG. 2i is a perspective view of a human leg from foot to knee and the compression bandage with completed application of the compression dressing with winding around the heel.
Figure 2A:
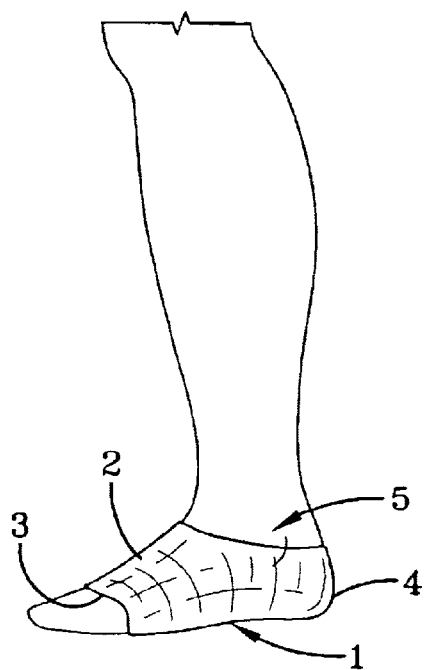
FIG. 2a is a perspective view of a human leg from foot to knee and the compression bandage without the compression dressing.
Figure 2B:
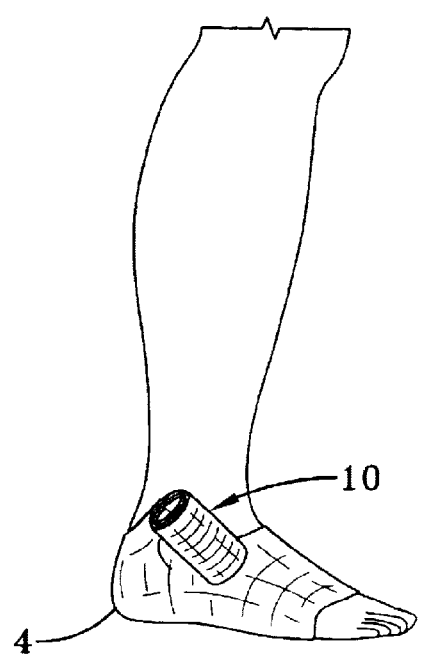
FIG. 2b is a perspective view of a human leg from foot to knee and the compression bandage with a first phase of application of the compression dressing by winding around the heel.
Figure 2C:
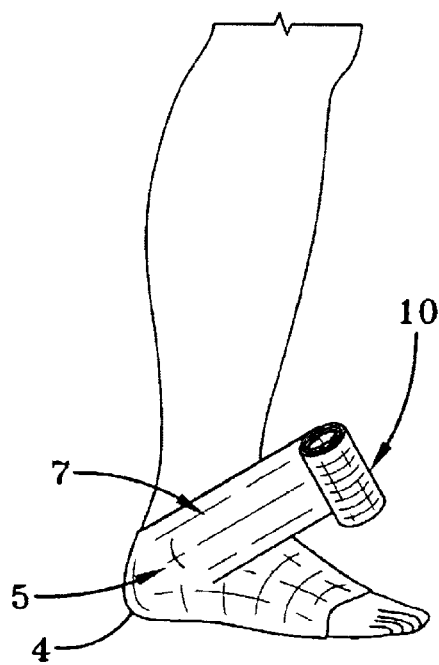
FIG. 2c is a perspective view of a human leg from foot to knee and the compression bandage with a second phase of application of the compression dressing by winding around the heel.
Figure 2D:
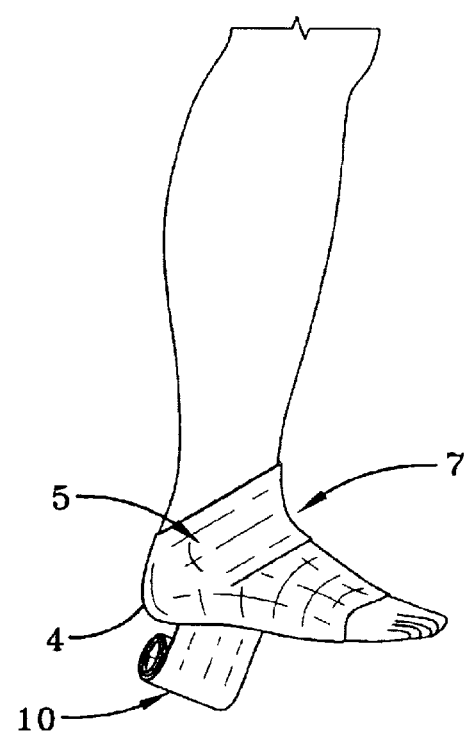
FIG. 2d is a perspective view of a human leg from foot to knee and the compression bandage with a third phase of application of the compression dressing by winding around the heel.

The application of the compression bandage according to the invention is extremely straightforward. First, the foot part 1 is pulled onto the foot in the manner of a stocking, as is shown in FIGS. 1a and 2a. Then, in accordance with subsequent FIGS. 1b through 1f, the dressing or roll bandage 10 arranged on the foot part 1 is wound on starting at the ankle area 5, and without going around the heel 4 again, preferably with ½ coverage of the dressing turns 6, in spiral formation or in figures of eight, and ending approximately two finger widths below the hollow of the knee according to the finished state shown in FIG. 1f.

Figure 2E:
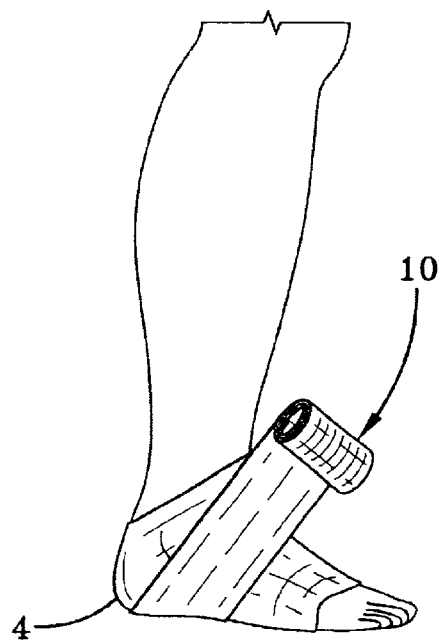
FIG. 2e is a perspective view of a human leg from foot to knee and the compression bandage with a fourth phase of application of the compression dressing by winding around the heel.
Figure 2F:
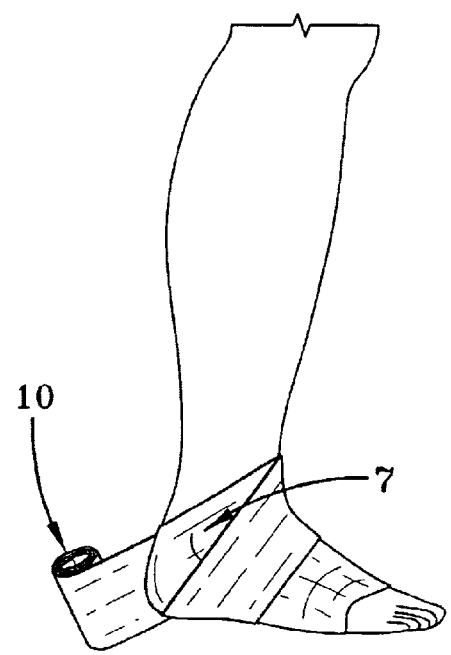
FIG. 2f is a perspective view of a human leg from foot to knee and the compression bandage with a fifth phase of application of the compression dressing with winding around the heel.
Figure 2G:
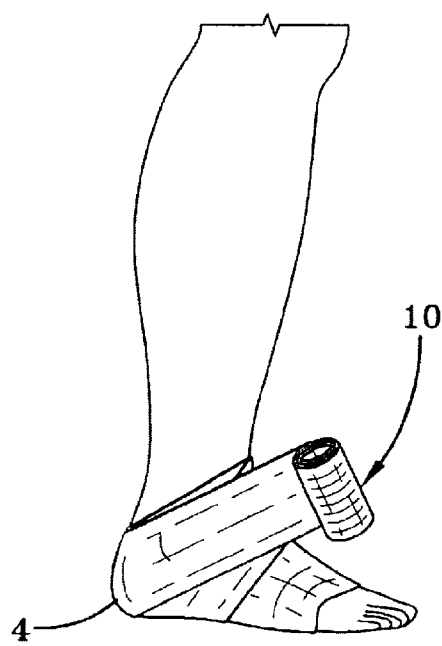
FIG. 2g is a perspective view of a human leg from foot to knee and the compression bandage with a sixth phase of application of the compression dressing with winding around the heel.
Figure 2H:
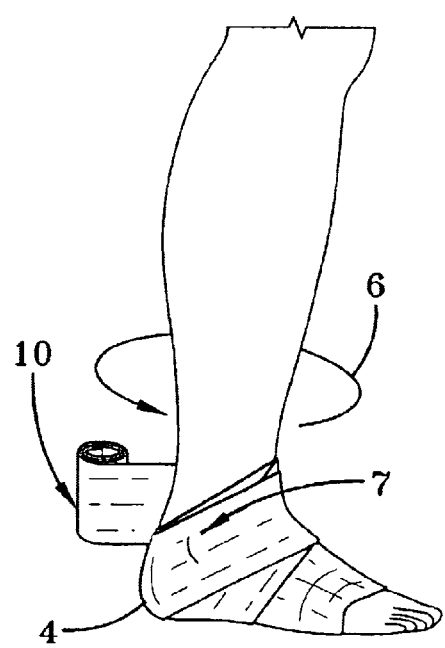
FIG 2h is a perspective view of a human leg from foot to knee and the compression bandage with a seventh phase of application of the compression dressing with winding around the heel.

FIGS. 2a through 2e show a similar procedure for application of the compression bandage according to the invention, which procedure differs solely in that after the foot part 1 has been pulled on, the dressing 10 is wound twice around the heel 4, as can be seen from FIGS. 2b through 2g. Here, the ankle joint 7 and the area 5 of the ankle are also wound and stabilized, as is necessary for example in the case of weakening of the ankle joint 17 caused by inflammation. Otherwise, the sequence of work phases for application of the compression bandage 10 according to the invention can be seen from the figures without further explanation. The leg after bandaging has been completed is shown in FIGS. 1f and 2e respectively.

Because of the straightforward handling on the one hand and because of the versatile use of a single product on the other instead of a previously used compression stocking and compression dressing, and due to its ability to be used even on varying calf circumferences, the invention is of great advantage and additionally results in considerable cost savings both for the patients and for those bearing the costs.

To this extent, the invention optimally achieves the object set out at the start.

The invention has been described with particular emphasis on the preferred embodiments, but variations and modifications within the spirit and scope of the invention may occur to those skilled in the art to which the invention pertains.

What is claimed is:

1. A compression bandage for supporting the tissue in the area between foot and knee, with a ready-made foot part comprising an open front without toe inclusion and an opposing upper edge, a circular-knitted compression middle part and a knitted-in heel, wherein a compression dressing attaches to the upper edge of the foot part, said compression dressing having a length of 3 to 7 meters.

2. The compression bandage as claimed in claim 1, wherein the foot part ends in the area of the ankle, specifically below or above the latter.

3. The compression bandage as claimed in claim 2, wherein the bandage is a combination of compression stocking and compression dressing.

4. The compression bandage as claimed in claim 1, wherein said bandage is a combination of compression stocking and compression dressing.

5. A method for treating venous and/or lymphatic leg swellings using a compression bandage for supporting the tissue in the area between foot and knee, said bandage having a foot part and a dressing, said method comprising:
   pulling the foot part onto the foot;
   winding the dressing onto the leg in a figure eight formation; and
   ending the winding about two finger widths below the hollow of the knee.

* * * * *